US009675491B1

(12) United States Patent
Seaman

(10) Patent No.: US 9,675,491 B1
(45) Date of Patent: Jun. 13, 2017

(54) HALLUX VALGUS BRACE

(71) Applicant: Anthony E Seaman, Redondo Beach, CA (US)

(72) Inventor: Anthony E Seaman, Redondo Beach, CA (US)

(*) Notice: Subject to any disclaimer, the term of this patent is extended or adjusted under 35 U.S.C. 154(b) by 128 days.

(21) Appl. No.: 14/049,763

(22) Filed: Oct. 9, 2013

Related U.S. Application Data

(63) Continuation-in-part of application No. 12/928,456, filed on Dec. 10, 2010, now abandoned.

(60) Provisional application No. 61/283,908, filed on Dec. 10, 2009.

(51) Int. Cl.
*A61F 5/00* (2006.01)
*A61F 5/01* (2006.01)

(52) U.S. Cl.
CPC ............ *A61F 5/019* (2013.01); *A61F 5/0127* (2013.01)

(58) Field of Classification Search
CPC ...... A61F 5/019; A61F 13/063; A61F 5/0127; A45D 31/00
USPC ........... 602/22, 30, 5; 128/893, 894; 132/73; D28/57
See application file for complete search history.

(56) References Cited

U.S. PATENT DOCUMENTS

| | | | |
|---|---|---|---|
| 1,055,810 A * | 3/1913 | Scholl | A61F 5/019 602/30 |
| 1,787,398 A * | 12/1930 | Sidgreaves | 602/30 |
| 2,066,443 A * | 1/1937 | Adams | A61F 5/019 601/27 |
| 2,069,034 A | 1/1937 | Hicks | 602/30 |
| 2,471,997 A * | 5/1949 | Baltor | 602/30 |
| 2,506,308 A * | 5/1950 | Maynier | 602/30 |
| 2,517,232 A | 8/1950 | Patulski | 132/73 |
| 3,110,306 A * | 11/1963 | Posner | 602/30 |
| 3,429,309 A | 2/1969 | Kurth | 602/30 |
| 3,550,593 A * | 12/1970 | Kaufman | 604/23 |
| 4,644,940 A | 2/1987 | Nakamura | 602/30 |
| 4,729,369 A * | 3/1988 | Cook | 602/30 |
| D344,367 S | 2/1994 | Santore | D28/61 |
| 5,282,782 A | 2/1994 | Kasahara | 602/30 |
| D352,115 S | 11/1994 | Kasahara | D24/192 |
| 5,437,616 A * | 8/1995 | Kasahara | A61F 5/019 128/894 |
| 5,453,083 A | 9/1995 | Kasahara | 602/30 |
| D393,931 S | 4/1998 | Rue | D28/57 |
| 6,093,163 A | 7/2000 | Chong et al. | 602/30 |
| D439,704 S | 3/2001 | Ikeda | D28/57 |
| 6,238,357 B1 * | 5/2001 | Kawaguchi | A61H 1/0266 128/DIG. 20 |
| 6,238,387 B1 * | 5/2001 | Miller, III | 606/34 |

(Continued)

FOREIGN PATENT DOCUMENTS

GB 43853 1 A * 11/1935
JP 2011122256 A * 6/2011

*Primary Examiner* — Kim M Lewis
(74) *Attorney, Agent, or Firm* — Jonathan A. Bay

(57) ABSTRACT

A hallux valgus brace has an L-shape with a downward, pry arm portion and a horizontal, lever arm portion. The pry arm portion inserts in the interspace between a wearer's big and second toe. The lever arm portion overlies the second and third knuckles of at least the second through fourth toes of the wearer. An applied force on the lever arm portion translates into a force against the big toe prying it from out and from under the wearer's second toe. The applied force is typically supplied by the wearer's shoe or sandal.

20 Claims, 24 Drawing Sheets

(56) References Cited

U.S. PATENT DOCUMENTS

| | | | |
|---|---|---|---|
| 6,318,373 B1 | 11/2001 | Kasahara | 128/894 |
| 6,964,645 B1 * | 11/2005 | Smits | A61F 5/019 |
| | | | 128/894 |
| 7,396,338 B2 * | 7/2008 | Huber | A61F 5/0102 |
| | | | 128/893 |
| 2004/0079670 A1 * | 4/2004 | Sendijarevic et al. | 206/523 |
| 2004/0225246 A1 * | 11/2004 | Doctor | 602/30 |
| 2005/0085756 A1 * | 4/2005 | Ferri | 602/30 |
| 2005/0251081 A1 * | 11/2005 | McClanahan et al. | 602/30 |
| 2006/0243291 A1 | 11/2006 | Daley | 132/73 |
| 2008/0005932 A1 * | 1/2008 | Zitin | 36/94 |

\* cited by examiner

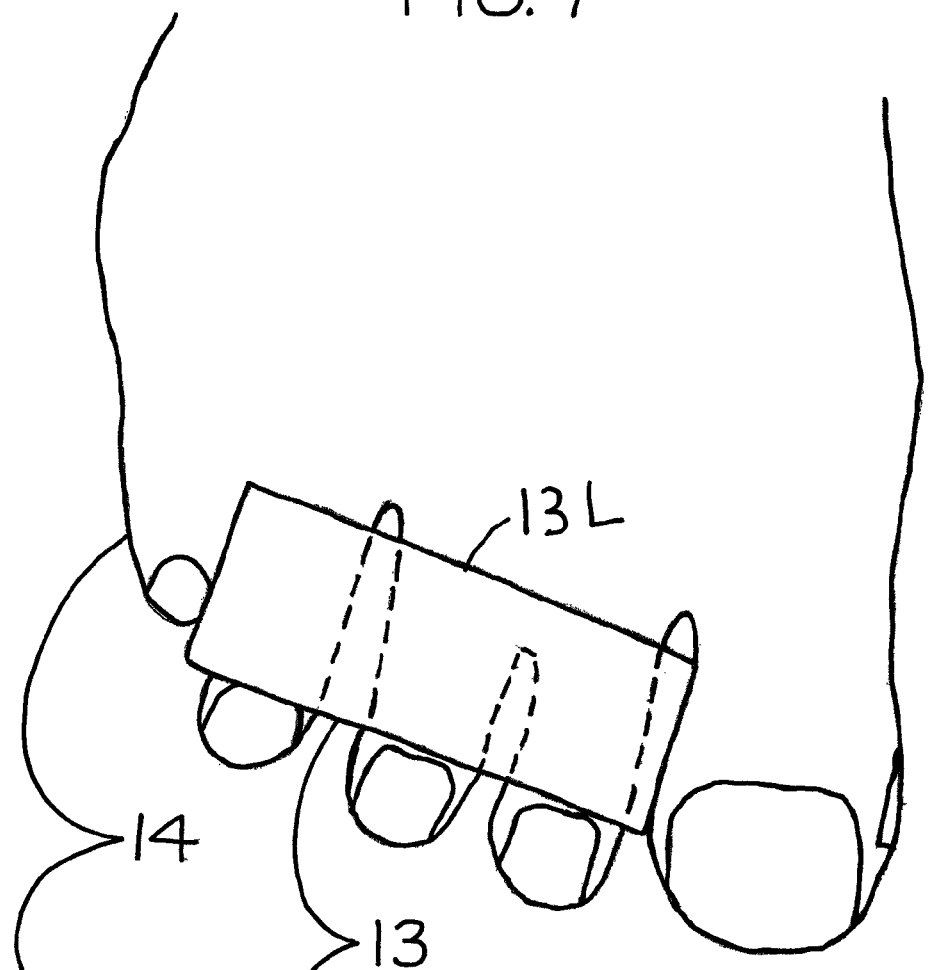

FIG. 11
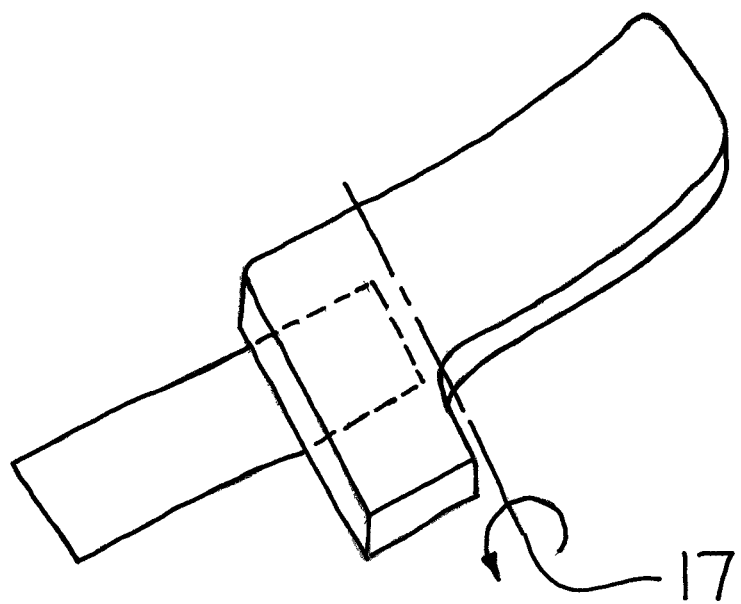
17
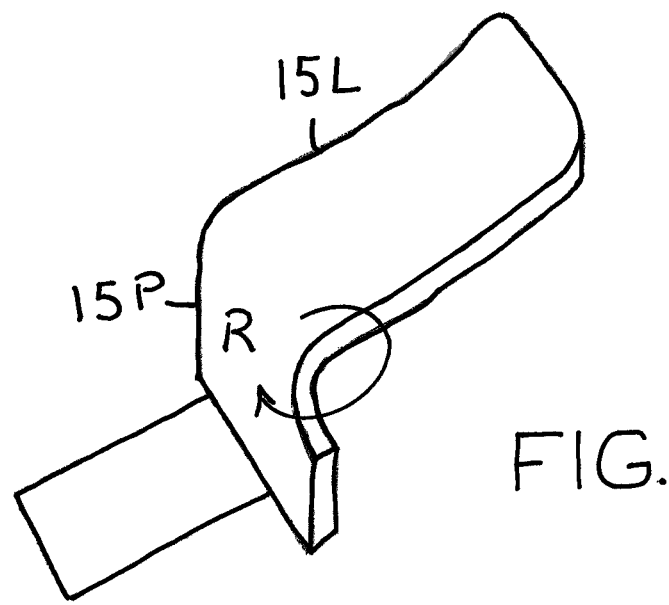
15L
15P
R
FIG. 12

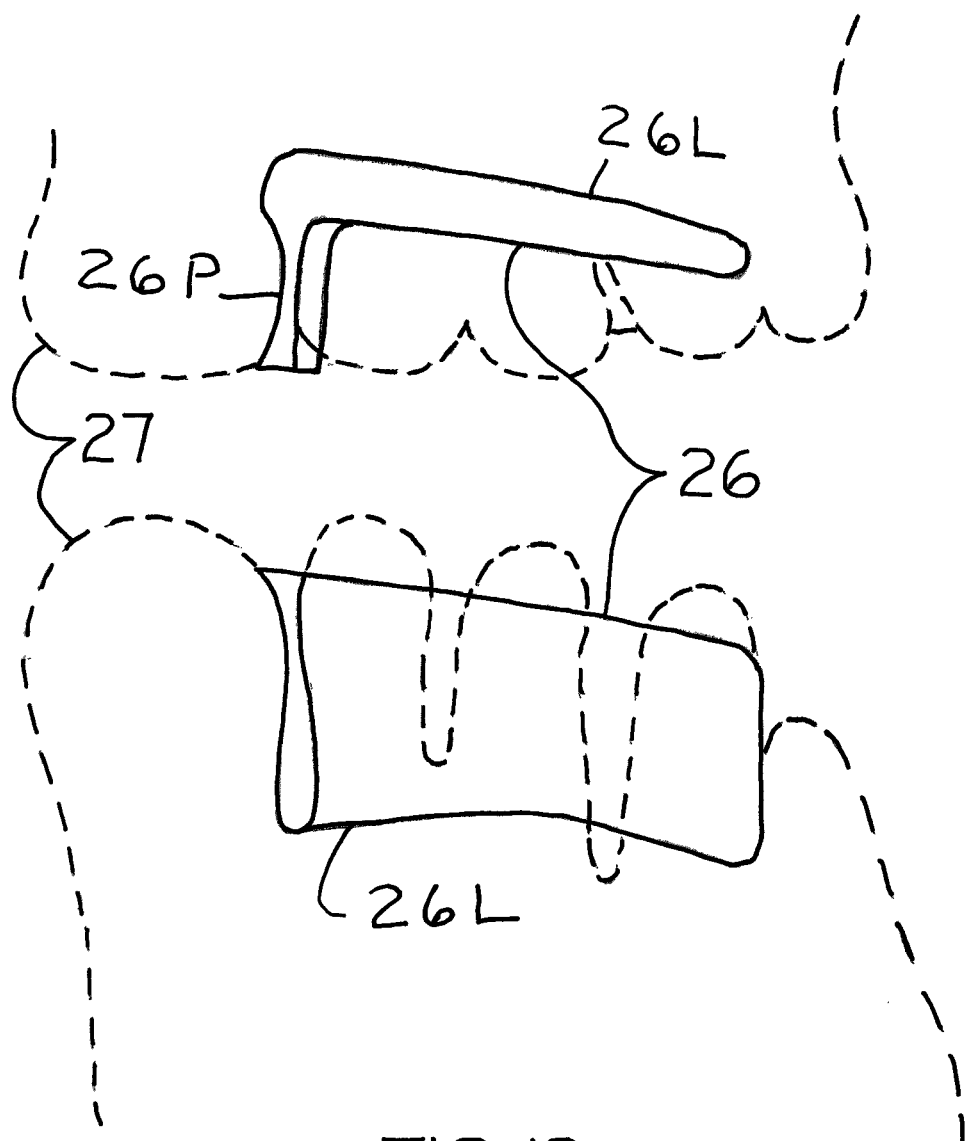

HALLUX VALGUS BRACE

CROSS-REFERENCE TO PROVISIONAL APPLICATION(S)

This application is a continuation-in-part of U.S. patent application Ser. No. 12/928,456, filed Dec. 10, 2010, which claims the benefit of U.S. Provisional Application No. 61/283,908, filed Dec. 10, 2009.

BACKGROUND AND SUMMARY OF THE INVENTION

The invention relates to orthopedic splints or braces and, more particularly, to a hallux (big toe) valgus (abnormal angulation) brace.

FIG. 1 shows a foot afflicted with both a bunion (1) on the big toe (Hallux Valgus) and hammer toes (2) on the other four. These deformities can happen individually but they often happen together as shown. The terms "hallux valgus," or "hallux abducto-valgus," are the most commonly used medical terms associated with a bunion anomaly, where "hallux" refers to the great toe, "valgus" refers to the abnormal angulation of the great toe commonly associated with bunion anomalies, and "abductus/-o" refers to the abnormal drifting or inward leaning of the great toe towards the second toe, which is also commonly associated with bunions. Note that, "hallux abducto" refers to the great toe moving away from the body's midline, and 'inward' to the second toe.

In FIG. 1, the big toe has slid under the second toe and the second toe never contacts the ground. There are many shortcomings with the prior art devices designed to straighten out the big toe, to correct hammer toes, or remedy both. Most don't work or are unsuitable for daily use. That is, most prior art devices aim to immobilize the big toe in a straight out stiffness, which is uncomfortable. The big toe needs to flex.

To understand the problem, a review of the bones of the foot is necessary. FIG. 2 shows the dorsal surface of the bones of the foot. The bones are divided into three groups:— the tarsus (3), the metatarsus (4), and the phalanges (5). When the foot is at rest (no load) the metatarsus bones keep a narrow profile. As a human stands up, a load is slowly applied to the foot, and the metatarsus bones fan apart from their base at the tarsus to make the foot wider. A wider foot provides more stability and it has lower unit area stresses than a narrow foot. As the load increases from dynamic activities such as walking, running or jumping, the bones fan apart even farther again to increase stability, to reduce the unit area stresses and to reduce shock. During the acts of walking, running or jumping, it is important to note that when the foot is lifted off of the ground, it returns to its narrowest width only to widen again when the foot is bearing the entire weight of the body.

The knuckles are the joints of the toes. The knuckles (6) at the base of the toes are where the metatarsus and the phalanges connect, at the ball of the foot, and may be referred to as the 1st or major knuckles. The knuckles at mid-toe are known as the 2nd knuckles ($6^2$) and 3rd knuckles ($6^3$) respectively. The pivot axes of the major or 1st knuckles (6) do not form a straight line. The smaller toes's major knuckles (6) pivot on an axis that sweeps along a gentle arc. The pivot axis for the big toe's major knuckle (6) is stepped back quite a step from the gentle arc of the smaller toes.

FIG. 3 shows a cutaway of the side of the foot with the tarsus and the metatarsus bones positioned for standing (7). During walking or running the toes remain flat on the ground and the tarsus and metatarsus pivot upward as shown (8). As the foot is pivoting upward, each toe is flexing upward (relative the plane of the metatarsals) at the pivot axis where the toe connects with its metatarsal, namely, its major knuckle (6). Since the pivot axes for the major knuckles (6) are far from a straight line, this causes the toes to fan apart, which increases stability.

When humans sleep (approx. 8 hours a day), the feet have no load and little movement. The remainder of the time (16 hours a day) the foot might be in constant movement with continual cyclic loading. It is the basic movement of the foot and differential movement between the bones (as described above) that most treatment devices and methods can not accommodate.

Some rigid devices tie to the base of the foot and use a lever to pull the big toe outward (ie., out from under the second toe, so, inward relative the body's midline). Most of these don't flex with the foot or do not fit in a shoe. And many of these immobilize the big toe in a straight out stiffness.

There are other devices that use an elastic bandage or sock to pull the big toe outward. But the big toe will return inward as the foot flexes during walking because the elastic becomes slack.

FIG. 4 shows how a spacer (9) placed between toes can easily become displaced during walking. This can happen even if the spacer is in a sock or attached to an elastic band.

The devices that attempt to manipulate the big toe outward by using the other four toes as a base, restrict the movement and bending of all the toes. As each of the phalanges and metatarsals move according to its load, these devices can not keep the big toe in its desired (corrected) position. Some use a rigid rod that runs under the toes and prevents the toes from laying flat on the ground. Any attempt to tie the toes together in the proper spacing fails because each toe bends independently and their major knuckles/pivot points (6) are not aligned with each other nor with the big toe. Most devices don't work and if they do, the user will experience pain and have a difficult time getting his/her foot into a shoe, and then a difficult time walking.

What is needed is an improvement over the shortcomings of the prior art.

BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the scope of the skills of a person having ordinary skill in the art to which the invention pertains. In the drawings.

FIG. 7 is a top view thereof shown worn on a foot;

FIG. 8 is a front view thereof;

FIG. 11 is a perspective view of a second embodiment of a hallux valgus brace in accordance with the invention, and shown flat in an unbent or un-flexed, "as manufactured" configuration;

FIG. 12 is a perspective view thereof shown in a formed (eg., flexed or bent) state as well as a wearer "worn" or "applied" configuration;

FIG. 17 is a front view of an alternate embodiment of a hallux valgus brace in accordance with the invention, and shown in a formed (eg., flexed or bent) state as well as a wearer "worn" or "applied" configuration;

FIG. 18 is a top view thereof;

DETAILED DESCRIPTION OF THE PREFERRED EMBODIMENTS

Figure 1:
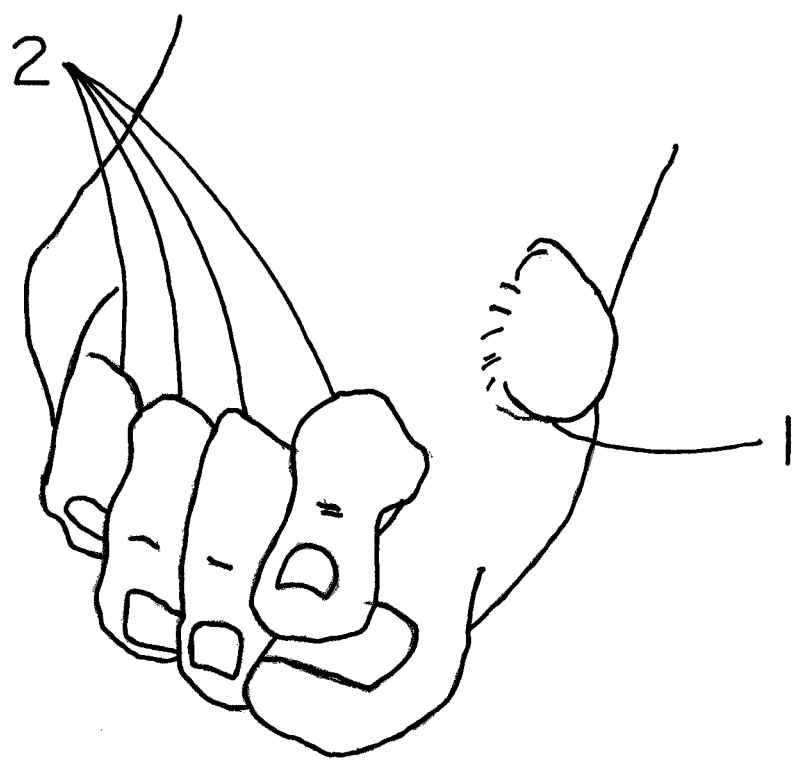
FIG. 1 is a perspective view of a foot.
Figure 5:
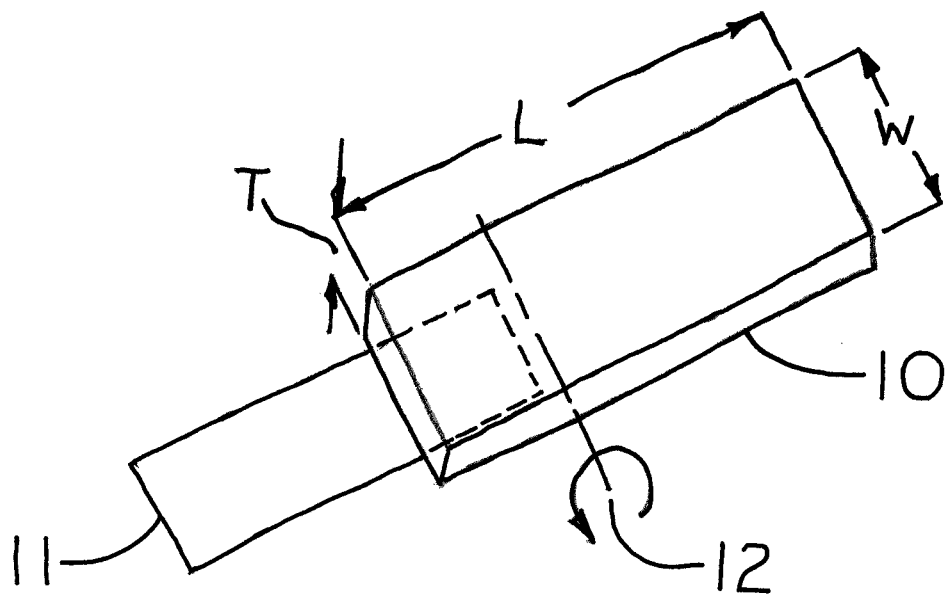
FIG. 5 is a perspective view of a first embodiment of a hallux valgus brace in accordance with the invention, and shown flat in an unbent or un-flexed, "as manufactured" configuration.
Figure 6:
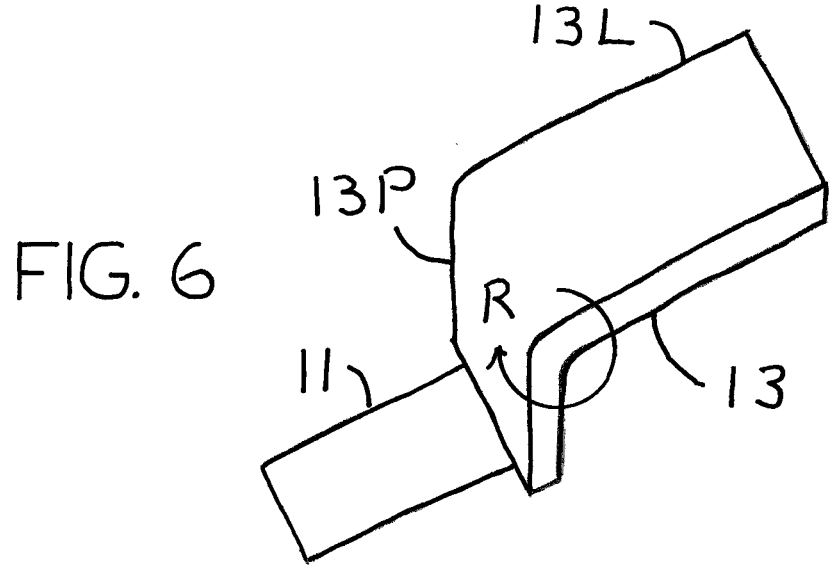
FIG. 6 is a perspective view thereof shown in a formed (eg., flexed or bent) state as well as a wearer "worn" or "applied" configuration.

FIGS. 5 and 6 show a strip of stock material (10) for forming into a hallux valgus brace (13) in accordance with the invention. The brace (13) is an economical device that, over time, will straighten out hammer toes into the same plane as the big toe, return a big toe to its correct position, and, diminish the size of a bunion as shown in FIG. 1. This brace (13) can also help urge the toes into proper position after an osteotomy, a bunionectomy or surgery to repair hammer toes.

The brace (13) comprises in its most basic form a rectangular strip (10) of foam, rubber, gel, etc. cut into a rectangular strip shape as shown. The thickness (T) preferably can vary upward from 0.06 inches (~1½ mm). The length (L) and width (W) can be personally tailored to suit each user. The foam, rubber, gel, etc. can be of any hardness and it can be infused with a skin softening agent, a fungicide or an anti-bacterial agent.

The strip (10) is flexed around the fold line (12) and held in place by hand, to get the final shape of the brace (13) as shown in FIG. 6. The brace (13) comprises an L-shape, comprising an elongated lever arm (13L) and an abbreviated pry arm (13P). Attached to the pry arm (13P) is a short piece of tape (11) to aid installation.

Again, FIG. 5 shows the hallux valgus brace (13) in a pre-formed configuration of being flat (1) in an unbent or un-flexed, or otherwise, in an "as made" configuration. Preferably, the flat strip (10) remains flat, unbent, or un-flexed until the occasion of wearing by the user/wearer. At that occasion, the user/wearer flexes the hallux valgus brace (13) to fit, or, approximately to the form shown by FIG. 6. This formed (eg., flexed or bent) state for the hallux vagus brace (13) has been formed, flexed or bent into wearer's "wearing" or "applied" configuration.

The material of the brace (13) is preferably a natural or synthetic rubber foam material or the like that has shape memory. That way, the lever arm (13L) and the abbreviated pry arm (13P) want to restore themselves to be co-planar with each other again. The wearer's shoes urge the lever arm (13L) down on the knuckles of the toes. The shape memory of the material of the brace (13) has the pry arm (13P) applying a restoring moment (indicated "R" in FIG. 6) on the wearer's big toe. Hence the lever arm (13L) is both forcing the toes in a plane in common with the big toe as well as bracing the pry arm (13P) for its lateral urge against the big toe to push it inward. The lateral urge supplied by the pry arm (13P) and lever arm (13L) to move the big toe to the inside is indicated as restoring moment (R) in FIG. 6.

Put differently, the restoring force to restore the big toe to an inward position, and from climbing on top of the second toe, is generated by the spring force of a flexed piece of flexible material flexed from a straight flat strip configuration and into an L-shape. Such a strip which is ordinarily flat but flexed into an L-shape naturally strains to un-spring and straighten itself out and, it is this spring force which in turn pushes the big toe inward.

This spring force generated by the strain to straighten itself (ie., strip 10, or brace 13) out is indicated in FIG. 6 as restoring moment (R). Brace (13) is designed to fit in a shoe and be worn during waking hours for walking or running. While worn in a shoe, the elongated lever arm (13L) rests on the knuckles of the hammer toes and forces them into the same plane as the big toe. Moreover, the elongated lever arm (13L) lacks inter-toe spacers for the second, third, fourth and pinky toes. Accordingly, such toes are neither fixed in position nor is the spacing among those toes fixed either. Hence the lever arm (13L) without such inter-toe spacers is comfortable to the wearer because the lever arm (13L) allows the foot and toes to spread out as the wearer walks or runs.

In brief, the brace (13) in accordance with the invention allows a foot to function normally (without too many constraints) while applying a restoring moment to the big toe as well as to the tops of the hammer toes to gradually straighten them out.

Figure 2:
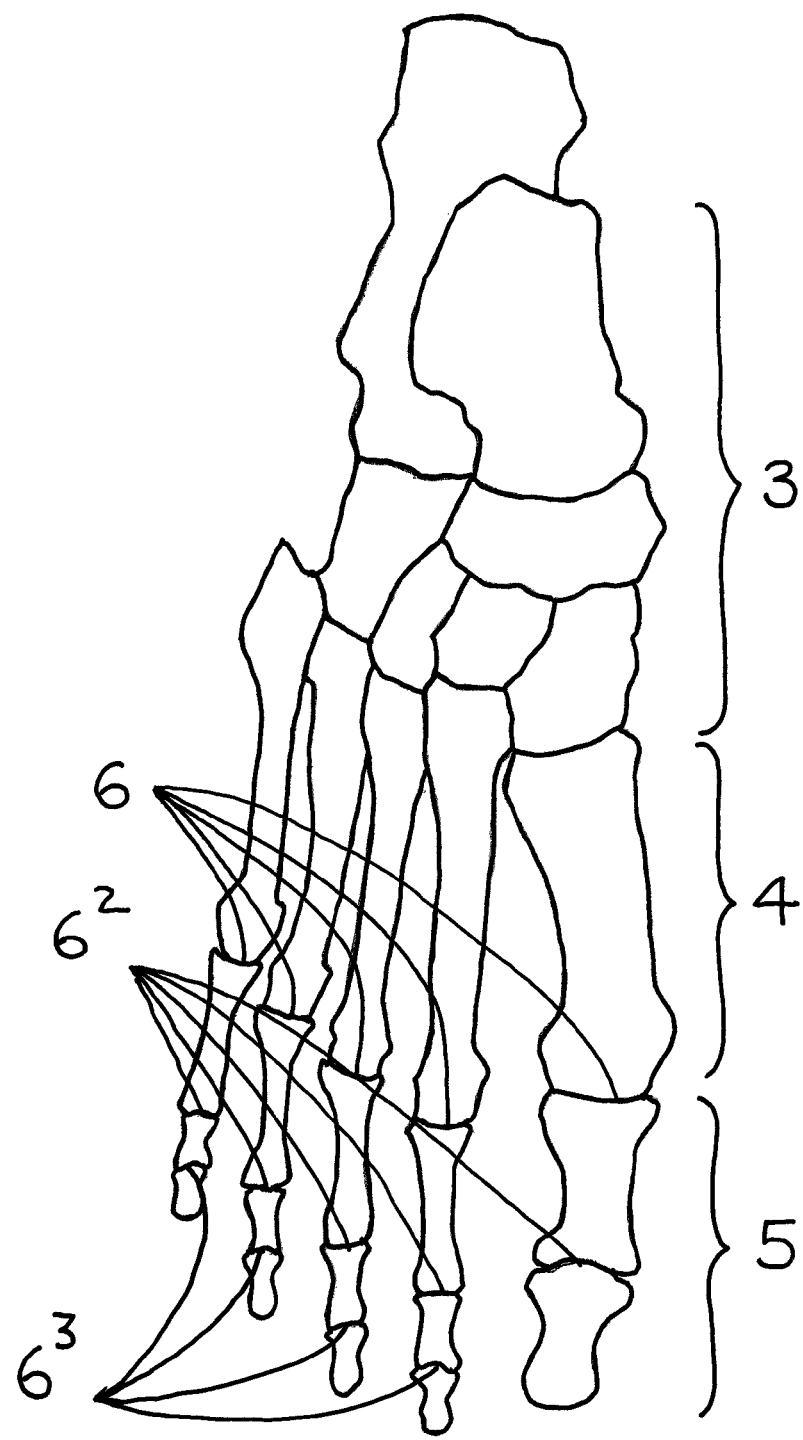
FIG. 2 is a plan view of the skeletal structure of a foot.
Figure 3:
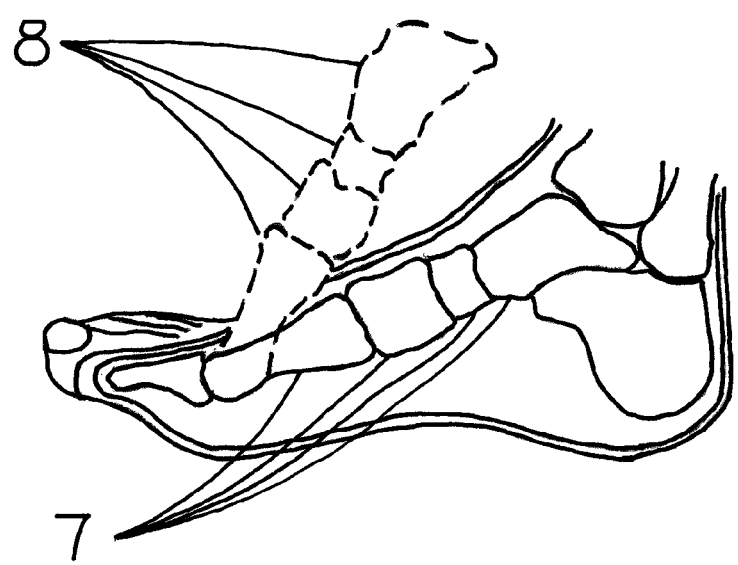
FIG. 3 is a side view of thereof.
Figure 4:
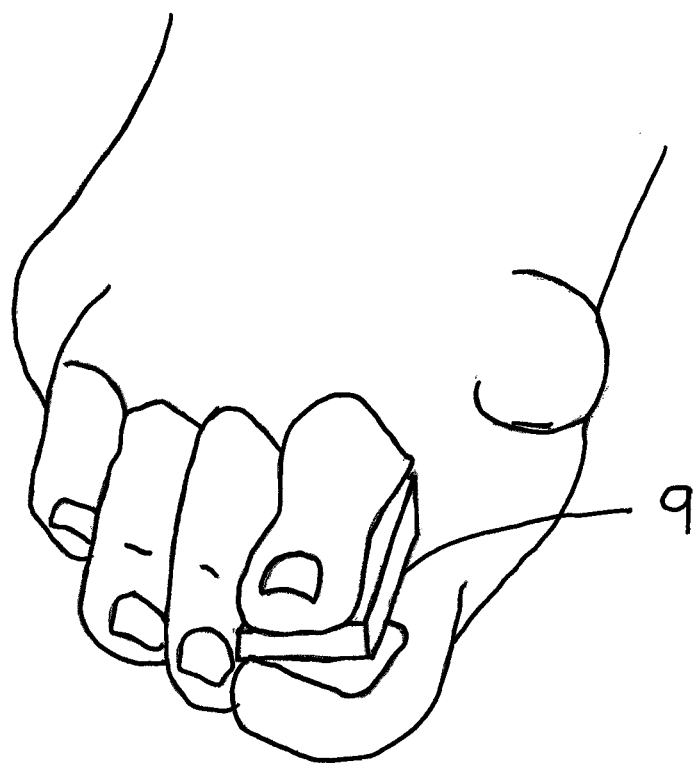
FIG. 4 is a perspective view of a spacer shown worn on a foot.

FIG. 7 shows a top view of the brace (13) as it sits on the foot (14). FIG. 8 shows the front view of the brace (13) as it sits on the foot (14). The pry arm (13P) fits between the big toe and the second toe and the lever arm (13L) rests on top of the second and third knuckles ($6^2$ and $6^3$) (and see FIG. 2) of the foot (14) as shown. The pry arm (13P) sits flush with the bottom of the big toe and the tape (11), which is optional, can be attached to the big toe as shown.

At this point in the installation, the pry arm (13P) of the brace (13) is held securely by the pressure between the toes with some aid from the tape. The lever arm (13L) of the "L" is held in place over the second and third knuckles ($6^2$ and $6^3$) of the toes by hand and the sock is carefully put over the foot and the foot is placed in the shoe. The shape memory of the material of the brace (13) has the pry arm (13P) applying a restoring moment (indicated "R" in FIG. 8) on the wearer's big toe.

Figure 9:
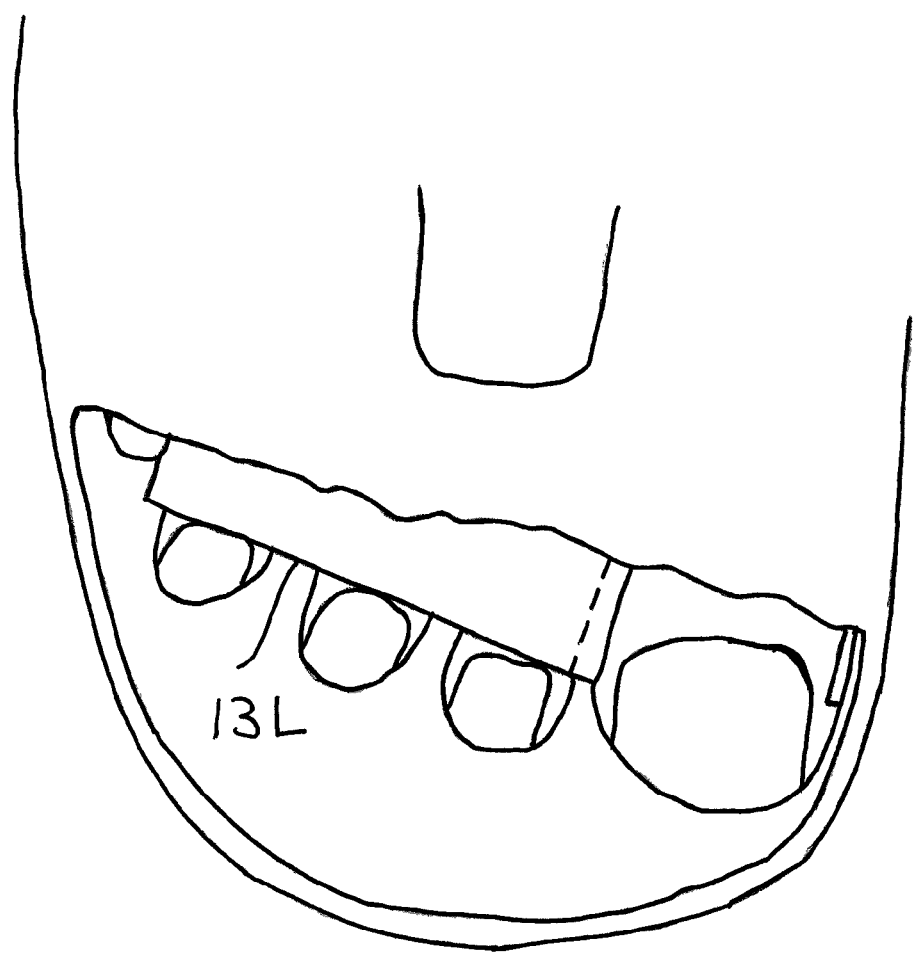
FIG. 9 is a top view thereof shown worn on a foot in a shoe, with portions of the top toe-cap of the shoe removed.
Figure 10:
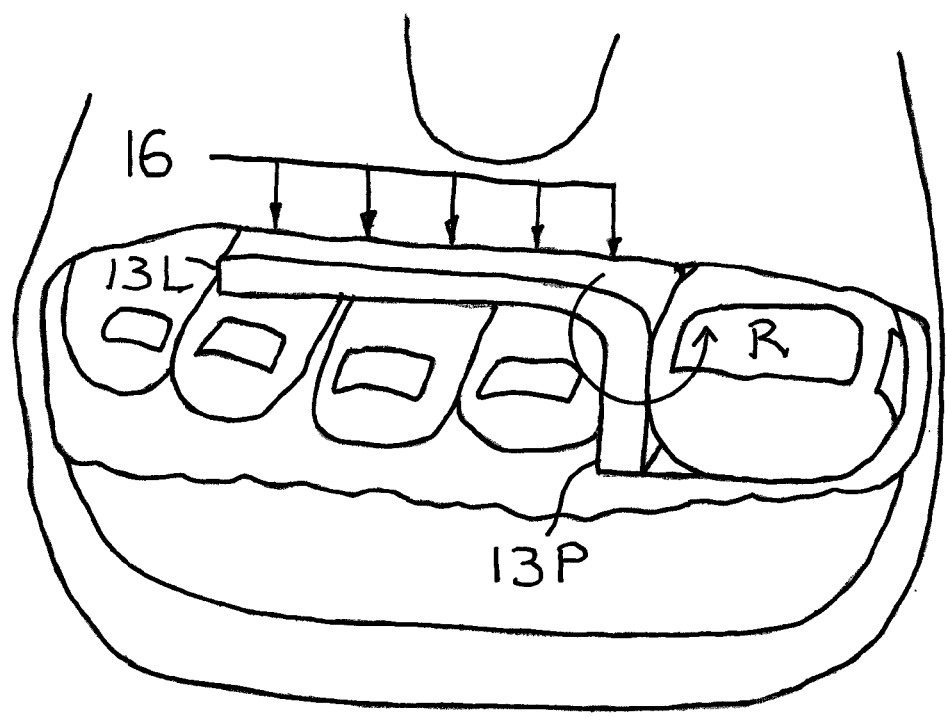
FIG. 10 is a front view thereof.

FIG. 9 is top view of the shoe with a cut away of the shoe and sock to show the relative position of the foot relative to the lever arm (13L). FIG. 10 is a front view of the shoe with the shoe and sock cut away to show the relative position of foot with the brace (13L,13P) attached. More importantly, it shows how the brace (13L,13P) works. The top of the shoe exerts a force (16) along the length of the lever arm (13L). More particularly, it is the toe portion of the shoe upper that exerts the force (16) along the length of the lever arm (13L).

Through the soft foam, the hammer toes are pushed down into the shoe in line with the big toe. The foam above the toes doesn't have to fit snugly. It should allow enough clearance for the toes to move freely from side to side.

The pry arm (13P) of the "L" puts a space (variable depending on thickness of foam) between the big toe and the second toe. This forces the big toe back toward its correct position. The shape memory of the material of the brace (13) has the pry arm (13P) applying a restoring moment (indicated "R" in FIG. 10) on the wearer's big toe. When the lever arm (13L) of the brace (13) is on the foot and in the shoe it needs nothing to hold it in place. The top of the shoe puts downward pressure on the lever arm (13L). The upward flexion of the foot at the major knuckles (6) keeps the brace (13L,13P) over the second and third knuckles ($6^2$ and $6^3$) of the toes.

The pry arm (13P) of the "L" is held in place by the pressure between the big toe and the second toe. Most importantly the brace (13L,13P) allows all of the relative movements between all the bones in the foot necessary for daily activities.

The process of straightening the toes will take time and can be accomplished using the brace (13L,13P) and slowly increasing the thicknesses of the foam in stages. The constant movement of the foot with the toes held in the right position will eventually change the shape of the foot.

FIG. 11 shows a stock piece of material that will be formed into a second embodiment of a hallux valgus brace (15L,15P) in accordance with the invention. The stock piece of material comprises a block-L outline of a piece of foam, rubber, gel, etc. that can be die cut at the factory or hand cut by an end user to a custom shape to better fit his/her foot. When the block-L outline of material is flexed or bent at the fold line (17) into an L-shape and held in place by hand, this gives the final shape of the brace (15L,15P) in FIG. 12. The shape memory of the material of the brace (15L, 15P) has the pry arm (15P) applying a restoring moment (indicated "R" in FIG. 12) on the wearer's big toe.

Figure 13:
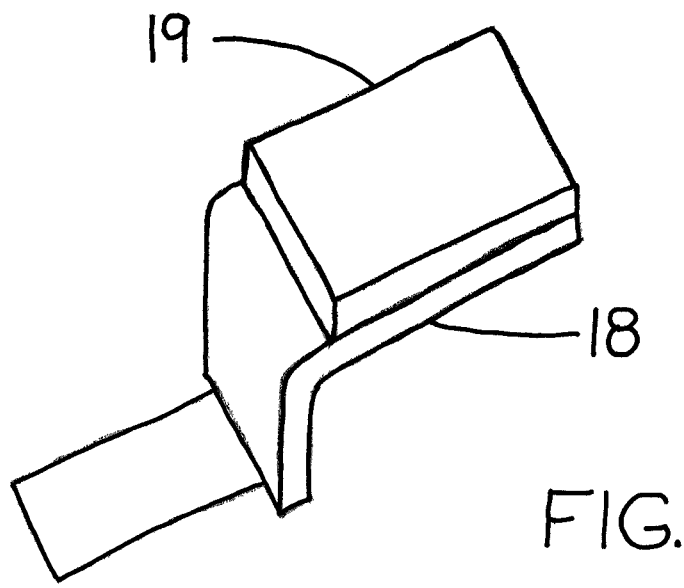
FIG. 13 is a perspective view thereof showing further construction of the hallux valgus brace shown in FIGS. 5-10, and shown in a formed (eg., flexed or bent) state as well as a wearer "worn" or "applied" configuration.

FIG. 13 shows a further construction of the hallux valgus brace (formerly 13, now 18) shown in FIGS. 5-10. In FIG. 13, the basic configuration of the brace (18) is shown with another smaller rectangular piece of foam, rubber, gel, etc (19) attached to it, that has double stick tape or glue to tailor the thickness of one of the lever arm, or pry arm, of the brace, but not the other. This promotes one of the goals of the method of use in accordance with the invention. That is, it is object of the use of the invention to build up the thickness of the lever arm portion of the brace (18) in accordance with the invention. The shape memory of the material of the brace (18) has the pry arm applying a restoring moment (indicated "R" in FIG. 13) on the wearer's big toe.

Figure 14:
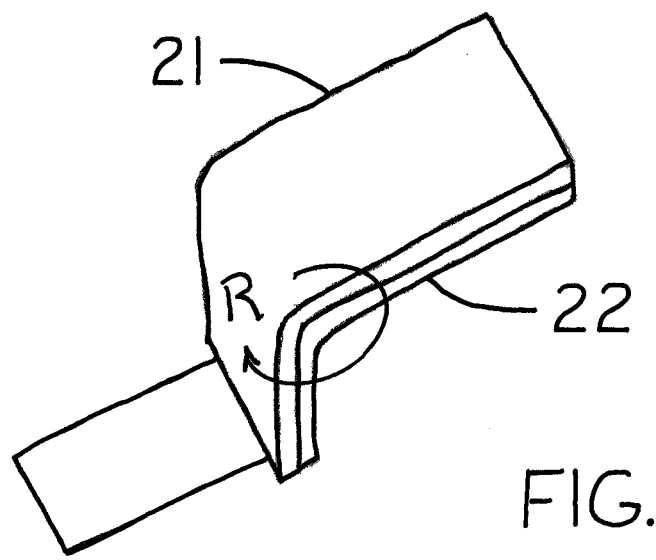
FIG. 14 is a perspective view thereof showing an alternate construction, and shown in a formed (eg., flexed or bent) state as well as a wearer "worn" or "applied" configuration.

FIG. 14 shows two different types of foam, rubber, gel, etc (21) (22) attached to one another with double stick tape or glue to create a composite of properties not available in one foam, rubber, gel, etc. The shape memory of the material of the brace (21,22) has the pry arm applying a restoring moment (indicated "R" in FIG. 14) on the wearer's big toe.

Figure 15:
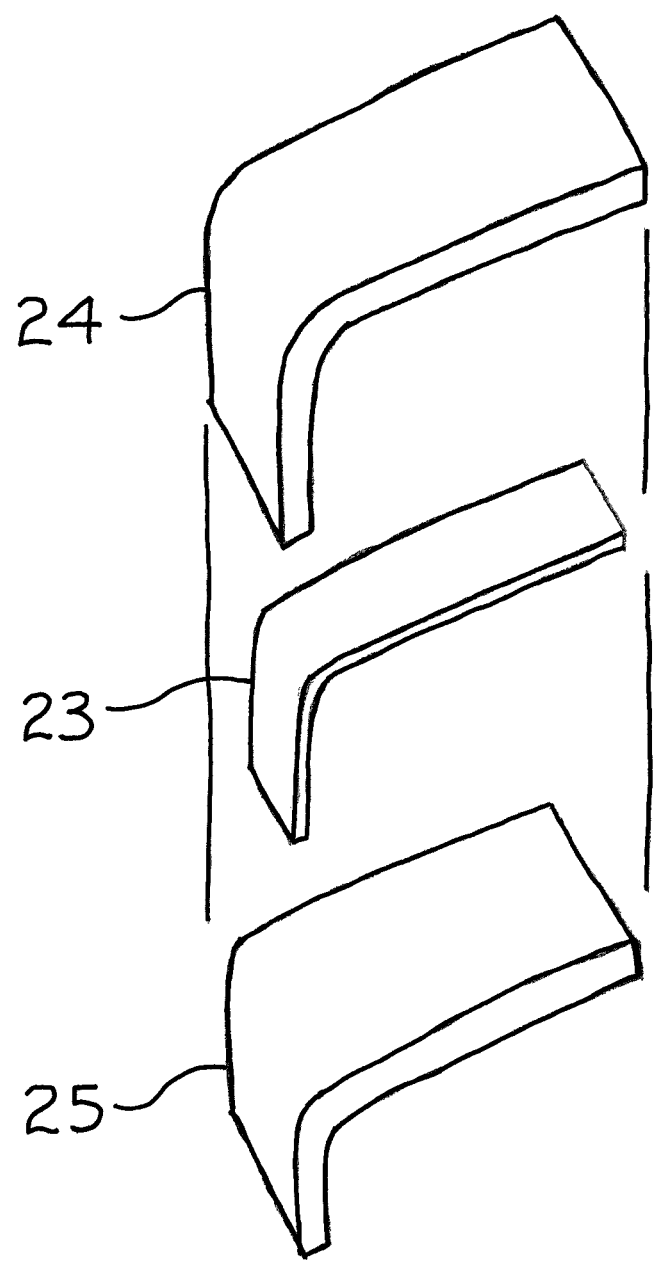
FIG. 15 is an exploded view thereof showing still another construction, and shown in a formed (eg., flexed or bent) state as well as a wearer "worn" or "applied" configuration.
Figure 16:
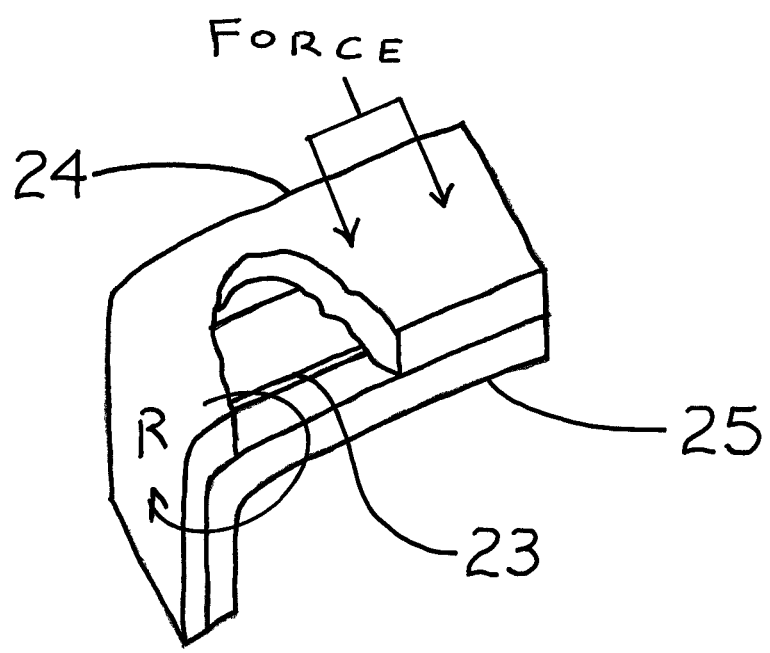
FIG. 16 is an assembly view thereof with portions broken away from the view to reveal interior structure, and shown in a formed (eg., flexed or bent) state as well as a wearer "worn" or "applied" configuration.

FIG. 15 shows an exploded view of a plastic or metal stiffening bracket (23) bonded between two different pieces of foam, rubber, gel, etc with glue or double stick tape. FIG. 16 shows the assembly (23,24,25) with a cutout to show the stiffening bracket (23). Preferably the metal stiffening bracket (23) has a light spring action to it, such that bracket (23) wants to straighten out from a flexed configuration, such that the spring action of the bracket (23) has the pry arm applying a restoring moment (indicated "R" in FIG. 16) on the wearer's big toe.

Otherwise, a stiff brace—in general—is not desirable.

All of the shapes shown above can be molded (including the brace (23,24,25) with the stiffening bracket (23) and the braces (18,19 or 21,22) with dual foam, rubber, gel, etc).

FIG. 17 is a front view of an alternate embodiment of a hallux valgus brace (26) in accordance with the invention. The brace (26) comprises a generally horizontal lever arm (26L) and a generally downward pry arm (26P). The pry arm (26P) has an hourglass shape to match the contour of the inter-toe space between the big and second toe, which enhances the big and second toes' traction on the pry arm (26P).

In FIG. 17, the brace (26) comprises a custom molded foam, rubber, gel, or the like so that it closely fits the shape of an inter-toe space between the big and second toes, as well as the knobbiness of the second and third knuckles on the tops of the toes. The silhouette of the foot is shown in dashed lines (27). FIG. 18 shows a top view of the custom molded brace (26).

Figure 19:
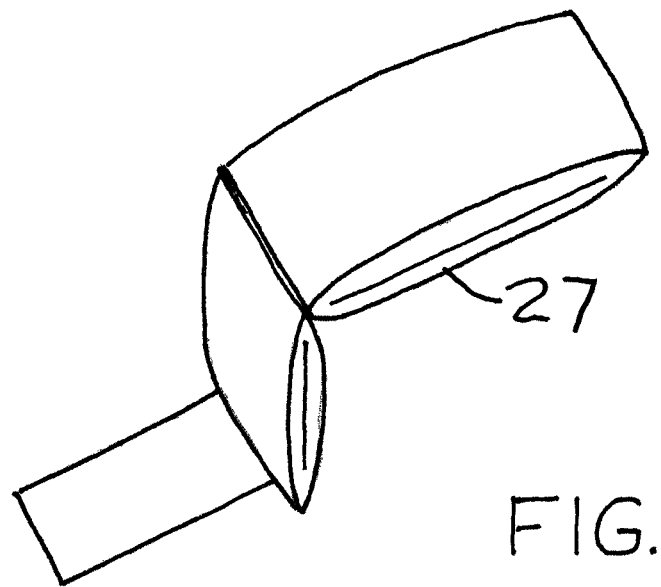
FIG. 19 is a perspective view of another embodiment of a hallux valgus brace in accordance with the invention, and shown in a formed state as well as a wearer "worn" or "applied" configuration.
Figure 20:
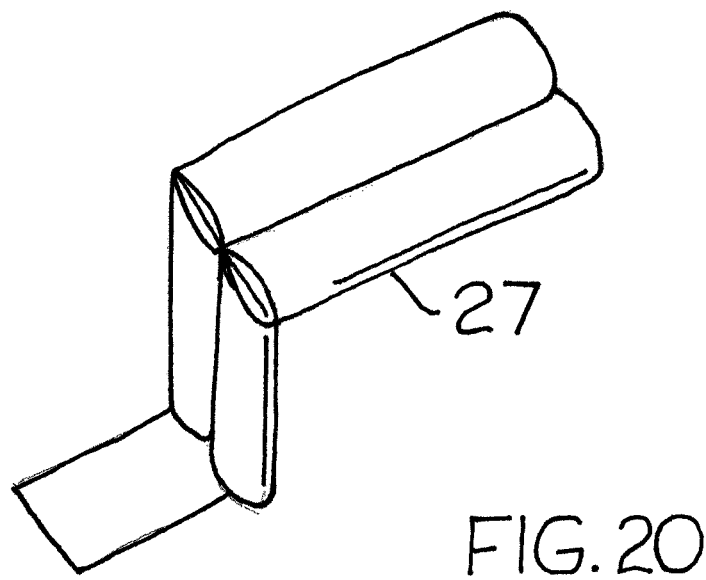
FIG. 20 is a perspective view of an alternate version thereof, and shown in a formed state as well as a wearer "worn" or "applied" configuration.

FIG. 19 shows another embodiment of a hallux valgus brace (27) in accordance with the invention, and shown formed. The FIGS. 19 and 20 brace (27) is preferably produced from multiple air filled bladders or chambers. The bladders can be constructed from soft flexible plastic or a similar material. Air filled bladders as shown in FIGS. 19 and 20 can be used in multiple configurations to achieve the desired cushioning. Air filled bladders can also be used in combination with top-coating or under-coating layers of foam, rubber, gel, etc as needed.

Figure 21:
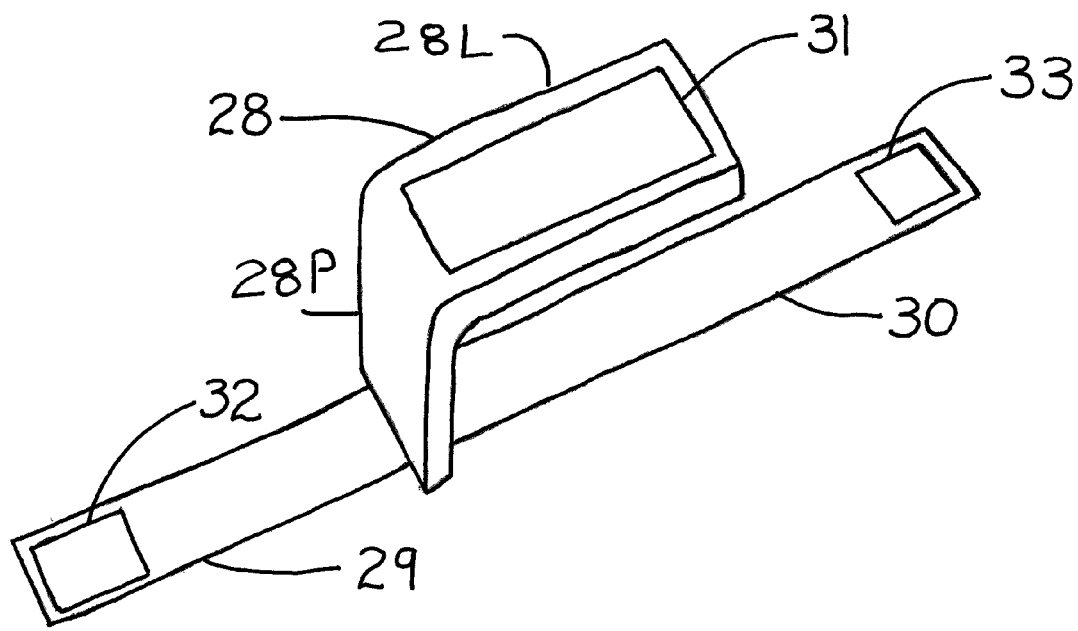
FIG. 21 is a perspective view of still a further embodiment of a hallux valgus brace in accordance with the invention, and shown in a formed (eg., flexed or bent) state as well as a wearer "worn" or "applied" configuration.
Figure 22:
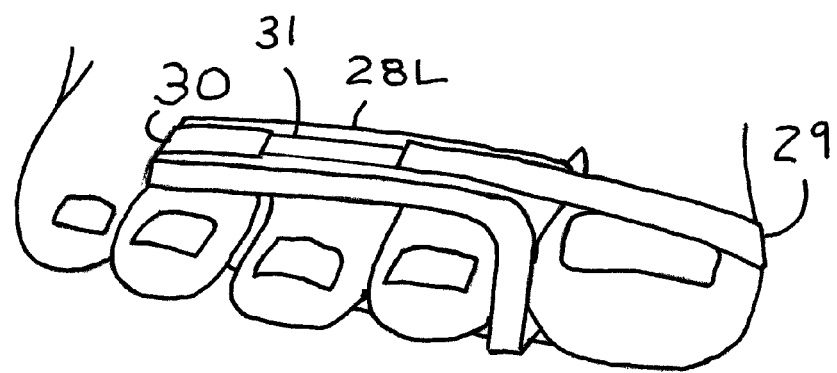
FIG. 22 is a front view thereof showing a manner of wearing.

FIG. 21 shows still a further embodiment of a hallux valgus brace (28) in accordance with the invention. FIG. 21 shows the brace (28) comprising a flexible strap having sections (29) and (30) attached to the pry arm (28P) as shown. On top of the lever arm (28L) of the brace (28) is a strip (31) of "hook" material of a hook- and pile fastener system (eg., VELCRO®). The strap sections (29) and (30) extend away from each other where they are commonly attached to the pry arm (28P) as shown. The strap sections (29) and (30) terminate in ends attached with patch of "pile" material (32) and (33). FIG. 22 shows how the strap sections (29) and (30) loop out from under the toes and are sized such that the patches (32) and (33) of pile material on the terminal ends of the straps (29) and (30) end up attaching to the strip (31) of hook material on the lever arm (28L) of the brace (28). This embodiment of the brace (28) works well when no shoes are available.

However, it is not a preferred embodiment when shoes are indeed available. The straps (32 and 33) tie the toes together and are painful. Accordingly, it is preferred to utilized strap (32) or strap (33) but not both when wearing shoes. Looking ahead to FIG. 26, the straps (132) therein are the better (and far less discomforting) way to tie the brace to the wearer's foot.

Figure 23:
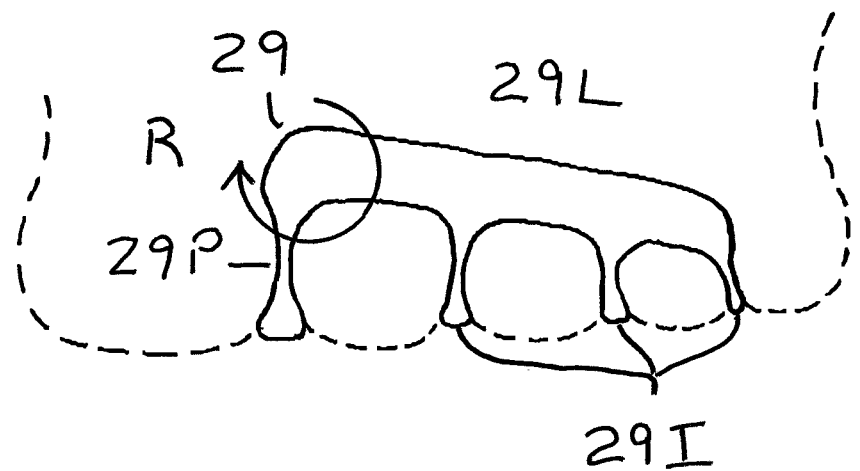
FIG. 23 is a front view of still another embodiment of a hallux valgus brace in accordance with the invention.
Figure 24:
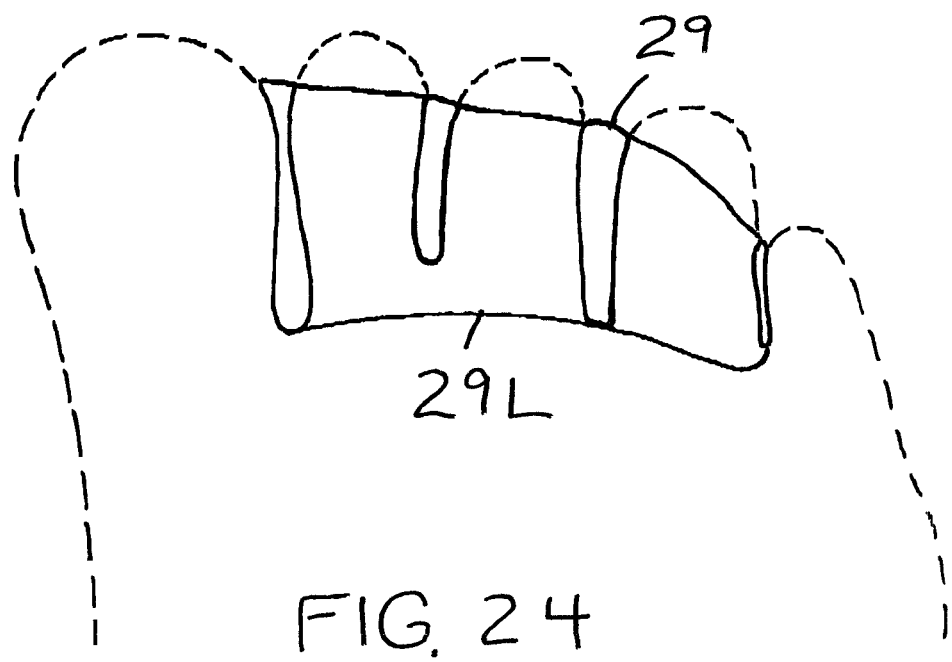
FIG. 24 is a top view thereof.

FIGS. 23 and 24 show still an additional embodiment of a hallux valgus brace (29) in accordance with the invention. The brace (29) comprises a lever arm (29L) and a pry arm (29P) and form fitting inter-toe spacers (291) extending off the lever arm (29L) sort of in symmetry with the pry arm (29P).

Preferably the brace (29) is cast or otherwise formed from a material that is not only cushiony for comfort but resilient too. That is, preferably the material once cast or milled has sufficient shape memory such that a cantilevered arm has a spring coefficient tending to induce the arm to return to original position if flexed. That way, the pry arm (29P) is pre-manufactured with an open angle relative to the lever arm (29L) that might be 100° (one-hundred degrees) instead of a right angle. That way, when a user/wearer installs the brace (29) on his or her foot, all he or she need to do is flex the pry arm (29P) a further 10° (ten degrees) to get the brace (29) to fit. The flexure of the pry arm (29L) by just 10° (ten degrees) will be sufficient to generate the restoring moment (R) on the big toe when the appropriate material properties are selected.

The pry arm (29P) and the form fitting inter-toe spacers (291) all have an dimples on the lateral faces thereof to match the contour of the lateral bulges of the insides of the toes. Hence these dimples in the lateral faces of the pry arm (29P) and the form fitting inter-toe spacers (291) enhance the form-fitting of the inter-toe space in which they are meant to fit.

Again, the big toe is not immobilized by the brace (29), but is pried away from out from underneath the second toe by the pry arm (29P). The brace (29) as a whole is stabilized in major part by applied forces on the top of the lever arm (29L) from the wearer's shoes and socks (or perhaps sandals). The brace (29) as a whole is stabilized in minor part by the traction of the toes on the dimple shapes on the lateral faces of the pry arm (29P) and form fitting inter-toe spacers (291). Additionally, the pry arm (29P) and form fitting inter-toe spacers (291) retain the lever arm (29L) from creeping up the wearer's foot above the major knuckles (6).

Figure 25:
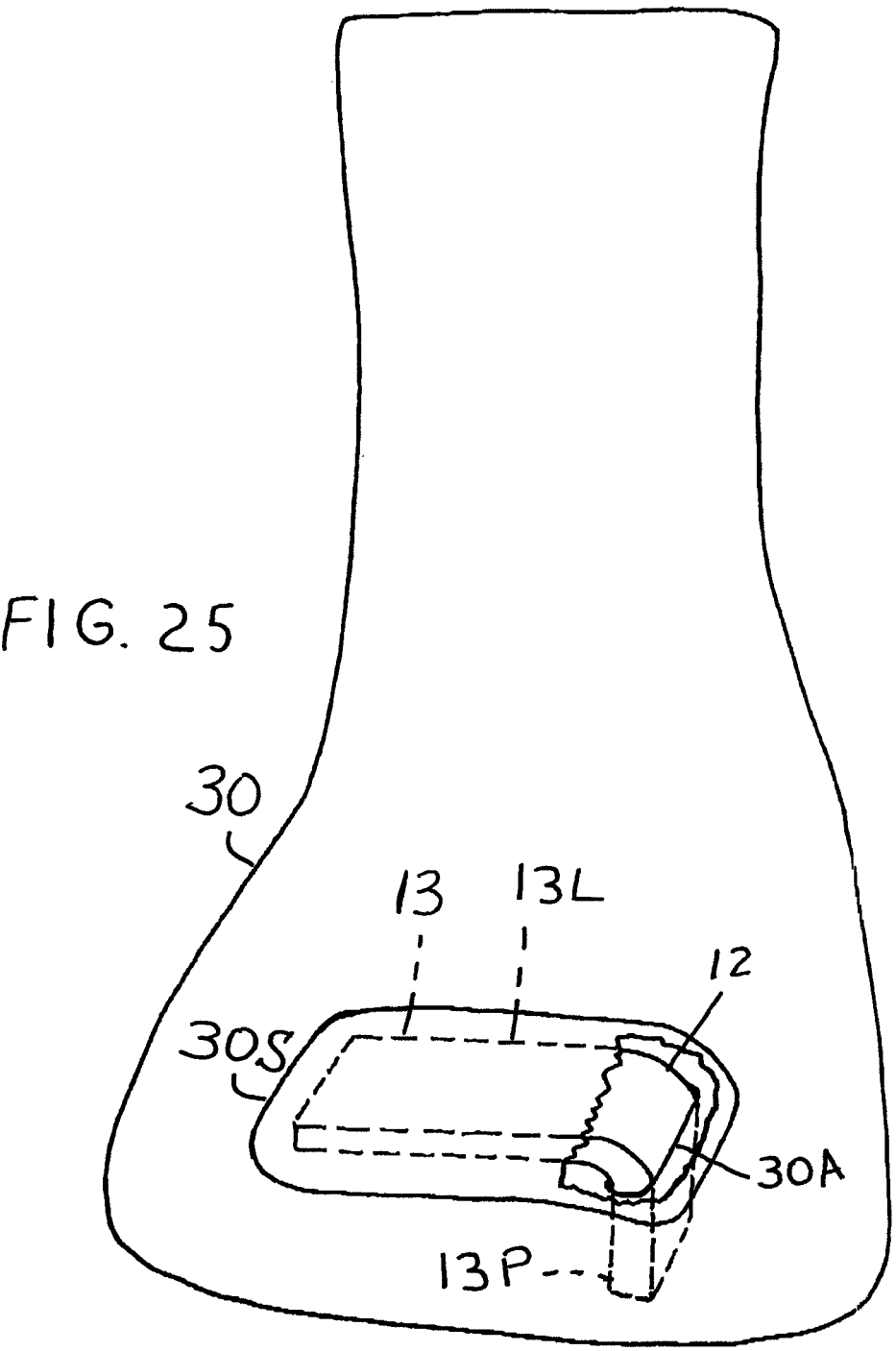
FIG. 25 is a perspective view of a combination sock with a hallux valgus brace in accordance with the invention, and shown in a formed (eg., flexed or bent) state as well as a wearer "worn" or "applied" configuration.

FIG. 25 shows a combination of a sock (30) in accordance with the invention with a representative hallux valgus brace (13) in accordance with the invention. The hallux valgus brace (13) has a lever arm (13L) and pry arm (13P) meeting at a fold line (12). The sock (30) has a sleeve (30S) sewn into the top of the inside of the sock (30). The sleeve (30S) is sized and configured to extend across the 2nd knuckles ($6^2$) and 3rd knuckles ($6^3$) of the wearer's toes. The sleeve (30S) has formed in it—or the sleeve (30S) and the sock (30) together form—an access slit (30A). This access slit (30A) is sized and configured to be located directly above the inter-toe space between the wearer's big and second toe. The lever arm (13L) of the brace (13) slides into the sleeve (30S) of the sock (30) through access slit (30A) until the fold line (12) is reached.

Hence the sock (30) with the appropriately placed and sized sleeve (30S) and access slit (30A) applies additional stabilizing, location, and retention forces on the brace (13). Again, the big toe is not immobilized. Any of the above braces above can be readily placed in the sleeve (30S) sewn into the sock (30). Alternatively, the braces themselves can be directly sewn into the sock (30). Any of the above braces can also be attached to the inside of a shoe or sandal.

In general, the braces should be soft and supple with little to no torsional rigidity on the lever arm of the brace that extends over the top of the toes. It is preferred that the material of the brace has a low coefficient of friction to avoid abrasions to the skin. The brace should not be over-constrained or attached to the toes or foot at multiple points or with tight straps or tape.

If a flat strip of foam or gel is used to form the brace in accordance with the invention, when it is flexed and placed in the shoe, the brace will have a spring like effect that will help push the big toe from out from under the second toe. This may be helpful in restoring the position of the big toe. The same type of spring effect may be obtained by biasing the angle between the lever arm and the pry arm of molded braces. Where metal or plastic stiffeners are used, they too can be biased to give the brace a spring like effect that pushes the big toe out from under the second toe. The lever arm of the brace can be contoured to fit the underside of the shoe's upper in the toe of the shoe. The lever arm can readily be contoured (eg., corrugated) to fit the knobbiness of the second and third knuckles of the second through fourth or fifth toes. The pry arm of the brace can be easily contoured to fit the big toe on one side and the second toe on the other. One example was the hourglass shape shown in FIG. 17. Another example were the opposite concavities of dimples for the lateral bulges of the insides of the big and second toe as shown in FIG. 23.

FIGS. 26 through 33 show additional embodiments of a hallux valgus brace (100) in accordance with the invention. In FIGS. 26 through 30, dimple (116) is intended for receiving the big toe, hence these views show a left foot configuration of brace (100), wherein the right foot configuration is a mirror opposite.

The brace (100) comprises a pry arm (102) and lever arm (104), and is shown in an un-flexed or unbent state prior to forming. That is, the brace (100) is shown prior to the flexing of or the bending over of the lever arm (104) to approximately a right angle, in the direction to the right. The flex (or fold or crease) line between the lever arm (104) and pry arm (102) is at the elevation of a notch (106). The notch (106) facilitates flexing or bending. The pry arm (102) and lever arm (104) comprise a unitary body or covering layer or outer shell (110) that covers an insert (112).

The covering layer (110) can be produced from single density foam or multiple density foam, open cell or closed cell, elastomer, gel, etc. The insert (112) is optional. If the outer shell (110) is manufactured from a soft (lower density) foam to aid in the cushioning of the toes, the insert (112) can be produced from a spring steel, a flexible plastic strip, a flexible composite strip, or a stiff (higher density) foam to increase the restoring moment (R) of the brace (100) on the big toe (eg., as similar to FIGS. 15 and 16). If the outer shell (110) is manufactured from a stiff (higher density) foam, the insert (112) can be dispensed with altogether. If kept in the manufacture of the brace (100), the insert (112) can be manufactured from a lower density foam, an air filled pocket (similar to FIGS. 19 and 20), a gel or liquid filled pocket (similar to FIGS. 19 and 20) or the like to allow the brace (100) to have extra suppleness or "give" and thus help cushion the toes. The insert (112) and brace (100) can be pre-manufactured with a bend at the crease line (eg., notch 106) to facilitate installation onto the foot. The degree of the bend is determined by the overall stiffness of the brace (100) and the wearer's tolerance to high restoring forces.

That is, if the insert (112) is made of spring steel and provided with a pre-manufactured bend, the angle of the bend might be 100° (one-hundred degrees) instead of a right angle. That way, when a user/wearer installs the brace (100) on his or her foot, all he or she need to do is flex the insert (112) a further 10° (ten degrees) to get the brace to fit. The flexure of the spring-steel insert (112) by just 10° (ten degrees) is sufficient to generate the restoring moment (R) on the big toe.

Given the foregoing, the outer shell (110) and insert (112) affords the manufacturer many diverse design combinations for tailoring the overall stiffness and/or cushiness of the brace (100).

The pry arm (102) is formed with an optional dimple (116) for the big toe and a corresponding dimple (118) for the index toe. The pry arm (102) further includes a base comprising an optional big toe angle stop (124) and an optional corresponding index toe angle stop (126). These angle stops (124,126) are preferably semi-rigid, and can be aluminum, steel, plastic, composite and so on. There is also an optional adhesive tape strip (128) for the big toe. These angle stops (124,126) are intended to impose a planar elevation for all the toes—big toe included—to have the toe pads of the toes line up on a reference ground plane. Additionally, the angle stops angle stops (124,126) prevent the tips of the big toe and the index toe from submarining under each other and the pry arm (102).

Moreover, there are optional adhesive tie straps (132) that are embedded in the covering layer (110) and fit between the wearer's toes. The tie straps (132) are adhered to underside of the wearer's foot and help hold the lever arm (104) over the knuckles of the wearer's toes. There optionally up to four such tie straps (132).

Figure 26:
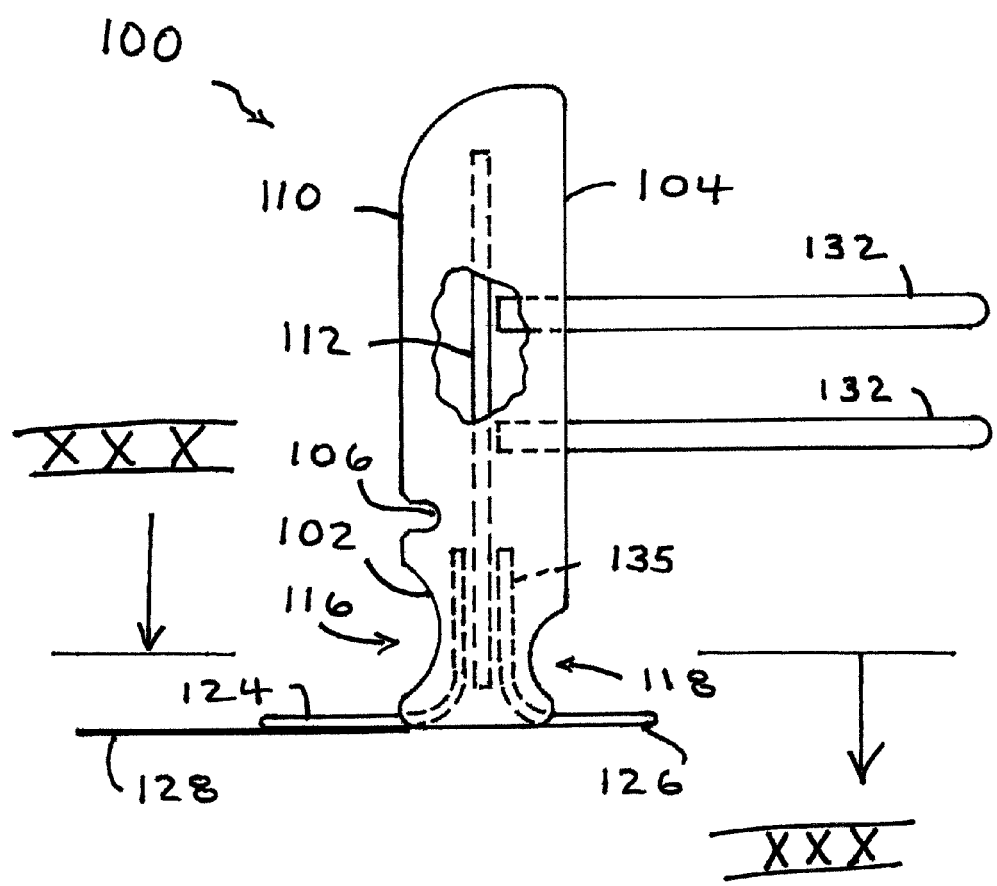
FIG. 26 is a front view of an additional embodiment of a hallux valgus brace in accordance with the invention, this brace being configured for a left foot, and shown flat in an unbent or un-flexed, "as manufactured" configuration (eg., bending or flexing the lever arm over to approximately a right angle, in the direction to the right, wherein the fold line between the lever arm and pry arm is at the elevation of the notch)
Figure 27:
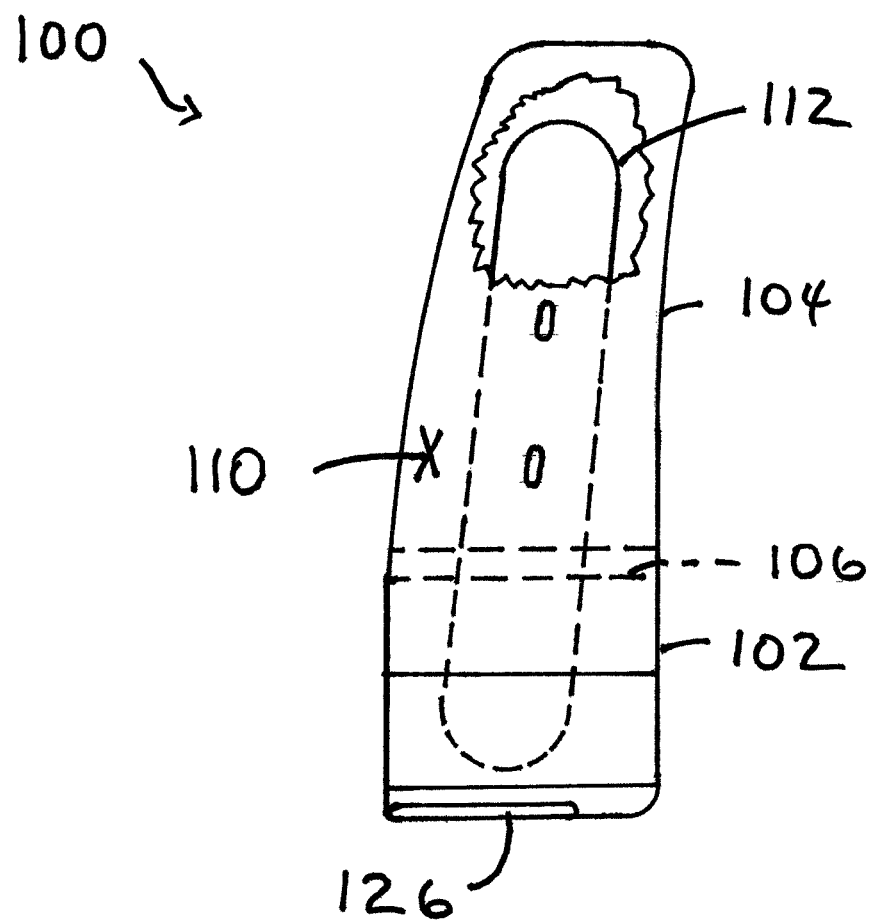
FIG. 27 is a right side view thereof.
Figure 28:
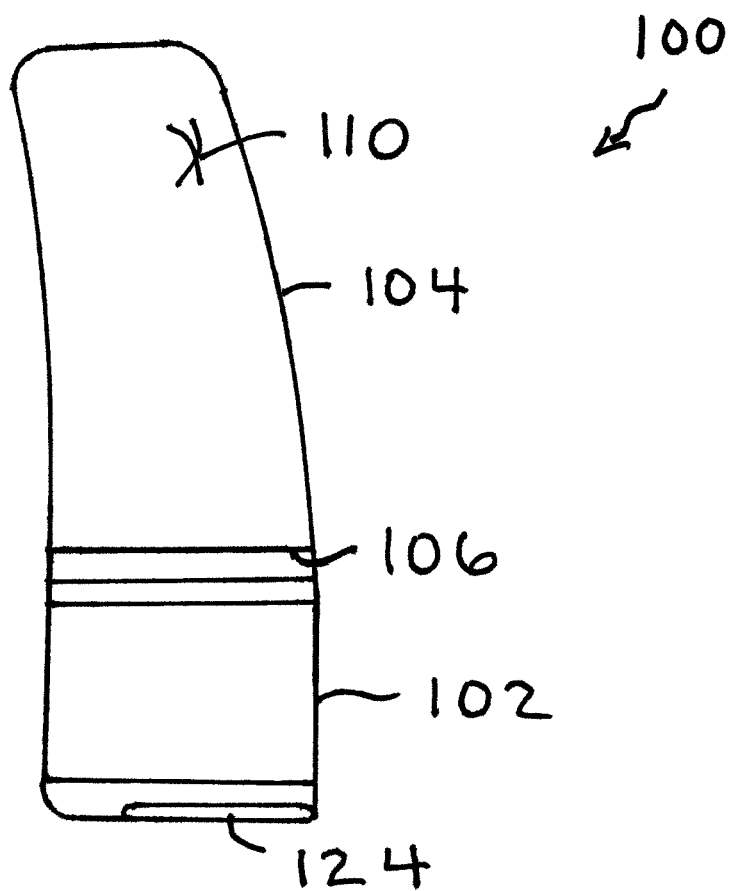
FIG. 28 is a left side view thereof.
Figure 29:
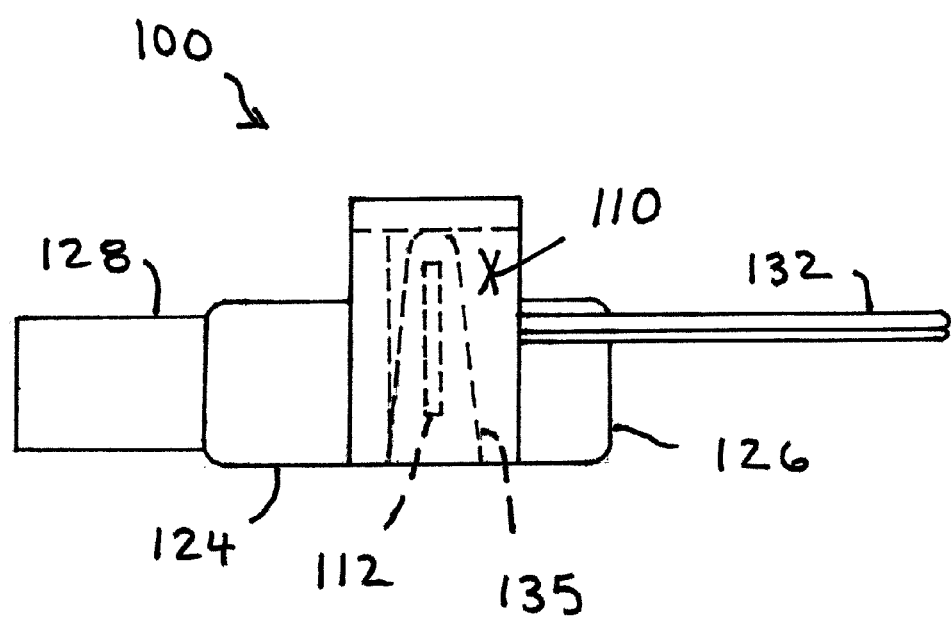
FIG. 29 is a top plan view thereof.
Figure 30:
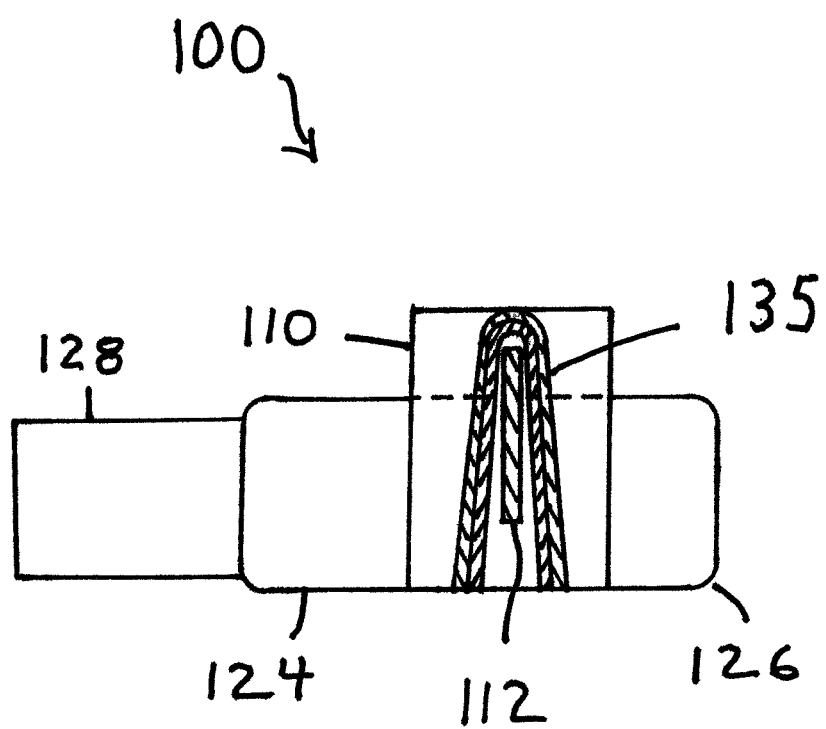
FIG. 30 is a section view take along line XXX-XXX in FIG. 26.
Figure 31:
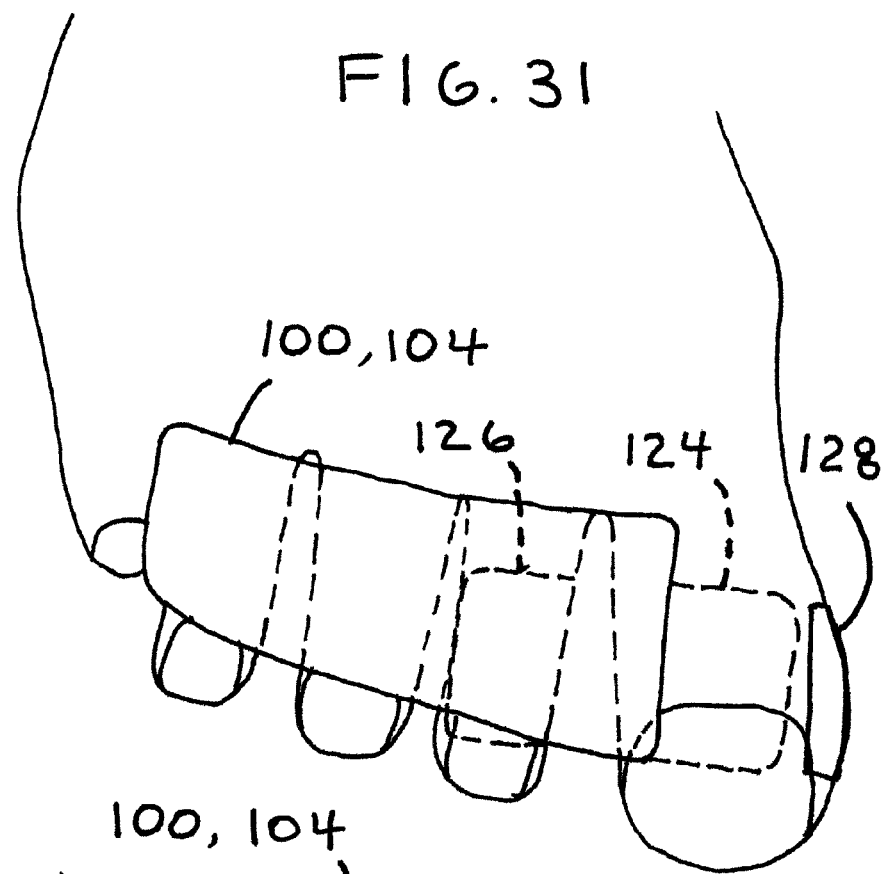
FIG. 31 is a top plan view of the FIGS. 26-30 embodiment of a hallux valgus brace in accordance with the invention as shown formed (eg., flexed or bent) and worn on a foot (albeit a right foot)
Figure 32:
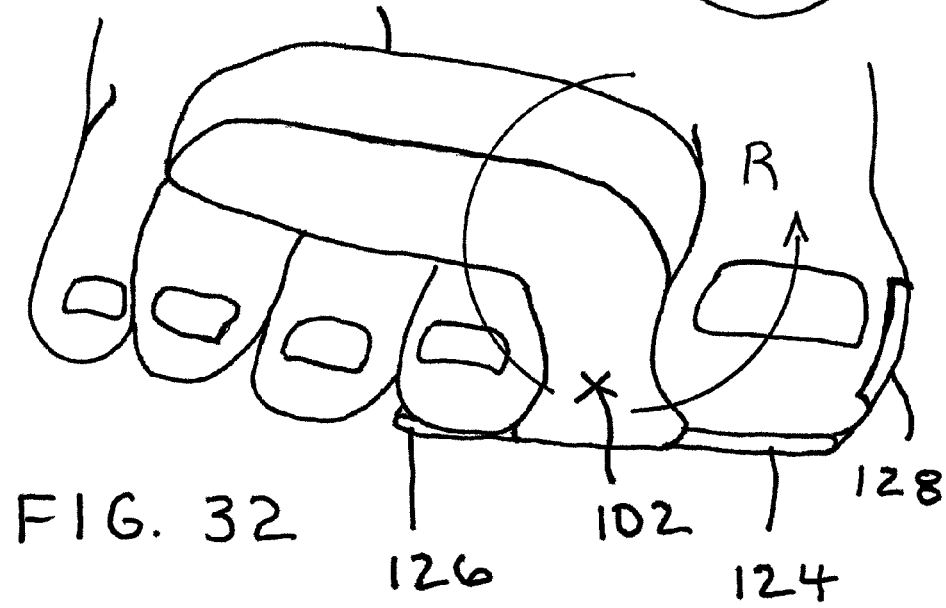
FIG. 32 is a front perspective view of the FIG. 31.
Figure 33:
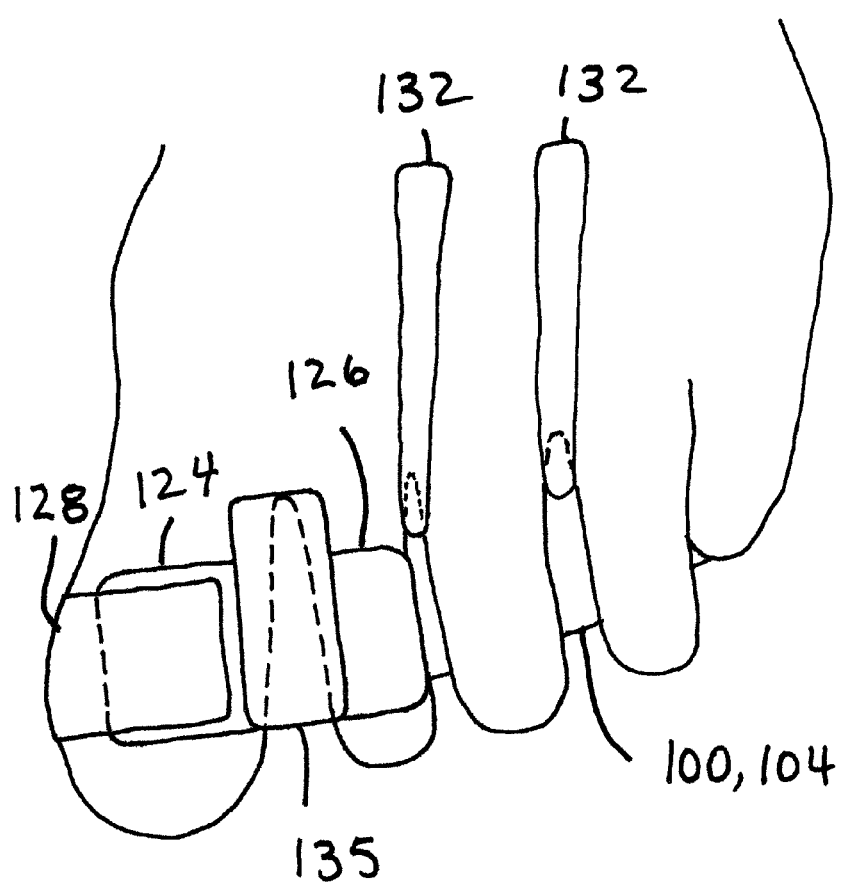
FIG. 33 is a bottom plan view of FIGS. 31 and 32.

FIGS. 26 and 30 show better that the big toe angle stop (124) and index toe angle stop (126) can be made of single piece or material, preferably plastic sheet, and meet in a U-shaped wedge form (135) that, when covered by the covering layer (110), forms the pry arm (102). The U-shaped form (135) acts as a spring between the big toe and index toe.

Hence the U-shaped form (135) adds an additional separating force between the big toe and index toe which adds to the restoring force generated by the spring force of a flexed piece of flexible material (102,104) flexed from a straight flat strip configuration and into an L-shape, which is straining to straighten itself out and which, in turn, pushes the big toe inward.

The bight of the U-shape form (135) can be filled with elastomer or the like to stiffen the springiness between the arms of the U-shaped form (135). The insert (112) can likewise emanate out of the bight of the U-shaped form (135) as well.

The restoring force in the majority of the embodiments disclosed above is generated by the spring force of a flexed piece of flexible material flexed from a straight flat strip configuration and into an L-shape, which is straining to straighten itself out and which, in turn, pushes the big toe inward. This is indicated in several of the views as restoring moment (R). Furthermore, the majority of the embodiments disclosed above are designed to fit in a shoe and be worn during waking hours for walking or running. While worn in a shoe, the elongated lever arm rests on the knuckles of the hammer toes and forces them into the same plane as the big toe. Moreover, in the majority of the embodiments above, the elongated lever arm lacks inter-toe spacers for the second, third, fourth and pinky toes. Accordingly, such toes are neither fixed in position nor is the spacing among those toes fixed either. Hence the lever arm without such inter-toe spacers is comfortable to the wearer because it allows for the foot and toes to spread out as the wearer walks or runs.

In brief, the braces in accordance with the invention allows a foot to function normally (without too many constraints) while applying a restoring moment to the big toe as well as to the tops of the hammer toes to gradually straighten them out.

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

I claim:

1. A hallux valgus brace to be worn on a user's foot inside a shoe having a toe cap; comprising:
    a spring device comprising a flat spring extending between a spaced pair of junctions with an elongated lever arm and an abbreviated pry arm respectively;
    said pry arm being configured to be interposed between a users' big toe and index toe;
    said lever arm being configured to be disposed overlying at least one knuckle of the user's index toe, middle toe and fourth toe, such that said lever arm receives downward urging from the toe cap of the shoe;
    said pry arm and lever arm having at least two relative configurations relative to each other, an un-flexed configuration and a flexed configuration in which the flat spring not only supports the pry arm as a cantilevered arm but is also flexed in opposition to a restoration force to the un-flexed configuration due to a spring coefficient for the flat spring;
    wherein the un-flexed configuration is characterized by, prior to any flexing forces applied to said brace, the pry arm and lever arm defining an angle between each other representing an open extreme;
    wherein the flexed configuration is characterized by the application of a flexing force between the pry arm and lever arm to close the angle representing the open extreme of the un-flexed configuration to an angle representing a flexed angle for the flexed configuration, with the pry arm interposed between the big toe and index toe, and with the shoe's toe cap urging down the lever arm which in turn urges down on the at least one knuckle of the user's index toe, middle toe and fourth toe; and wherein, because of the restoration force due to the spring coefficient of the flat spring, the pry arm applies an inward restoring force against the big toe as a result of seeking to restore said brace to the un-flexed configuration.

2. The hallux valgus brace of claim 1 wherein:
in the flexed configuration, the lever arm extends from the respective junction therefor with the flat spring to a distal edge as the pry arm extends from the respective junction therefor with the flat spring to a lower edge.

3. The hallux valgus brace of claim 2 wherein:
the pry arm that has a height extending between the respective junction therefor with the flat spring and the lower edge, a width extending between fore and rear edges, and a lateral thickness extending between spaced lateral faces;
wherein the pry arm's width and thickness are sized for insertion in an interspace between the user's big and second toe, and the pry arm's height is sized such that the lower edge is about level with a toe pad of the user's big toe with the upper extreme clearing the level of a top of the second toe; and
the lever arm has a length extending between the respective junction therefor with the flat spring and the distal edge, a width extending between fore and rear edges, and a thickness extending between spaced upper and lower surfaces;
wherein the lever arm is sized and configured relative to the pry arm such that the lever arm overlies the second and third knuckles of at least the index through fourth toes of the user, whereby an applied force on the lever arm's upper surface translates into an inward force applied against the big toe thereby prying the big toe out and from under the user's second toe.

4. The hallux valgus brace of claim 3, wherein:
the rear edges of both the pry arm and lever arm cooperate with the web between the user's big and second toe as well as with the flexion of the user's foot at the major knuckles while walking to retain the lever arm located over the user's second and third knuckles of at least the second through fourth toes, and not rearward of the major knuckles.

5. The hallux valgus brace of claim 3, wherein:
the pry arm's lateral faces are configured in an hour glass shape to better form fit the contours of the insides of the big and second toes and thereby promote positional stability.

6. The hallux valgus brace of claim 3, wherein:
the pry arm's lateral faces are configured with dimples to better form fit the contours of the insides of the big and second toes and thereby promote positional stability.

7. The hallux valgus brace of claim 2 wherein:
the lever arm, flat spring and pry arm in combination comprise a unitary, single-piece of an elongated flat spring material extending through all of the lever arm, flat spring and pry arm as between, in the flexed configuration, the distal edge of the lever arm and the lower edge of the pry arm.

8. The hallux valgus brace of claim 7 wherein:
said unitary, single-piece of an elongated flat spring material comprises a single strip of spring steel.

9. The hallux valgus brace of claim 7 wherein:
said unitary, single-piece of an elongated flat spring material comprises a single piece of any of a flexible plastic strip, a flexible composite strip, or a natural or synthetic rubber foam material.

10. The hallux valgus brace of claim 1 wherein:
in the un-flexed configuration, the angle representing the open extreme between the lever arm and pry arm is about 100° and which in the flexed configuration, the flexed angle is about 90°.

11. The hallux valgus brace of claim 1 wherein:
in the un-flexed configuration, the lever arm and pry arm are about co-planar with each other, and in the flexed configuration, the flexed angle is about 90°.

12. The hallux valgus brace of claim 1 wherein:
in the un-flexed configuration, the lever arm and pry arm range from being about co-planar with each other to sub-tending an angle of about 100° relative to each other, and in the flexed configuration, the flexed angle is about 90°.

13. The hallux valgus brace of claim 1 wherein:
the lever arm, flat spring and pry arm in combination comprise a common composite structure comprising an insert (112) and a covering layer (110) that covers the insert (112) and which composite structure extends through all of the lever arm, flat spring and pry arm;
wherein said insert (112) is the material that provides the flat spring with the spring coefficient therefor; and
wherein said insert (112) extends in one direction from the flat spring as a component of the pry arm, and, in the other direction as a component of the lever arm.

14. The hallux valgus brace of claim 13 wherein:
the covering layer (110) is produced from a soft (lower density) foam to aid in the cushioning of the toes; and
the insert (112) is produced from a spring steel, a flexible plastic strip, a flexible composite strip, or a stiff (higher density) foam to increase the restoring moment (R) of the brace (100) on the big toe.

15. The hallux valgus brace of claim 13 wherein:
the covering layer (110) is produced from a stiff (higher density) foam; and
the insert (112) is produced from a lower density foam, an air filled pocket, a gel or a liquid filled pocket whereby to provide the brace with extra suppleness or "give" and thus help cushion the toes.

16. The hallux valgus brace of claim 13 wherein:
in the un-flexed configuration, the insert (112) is made with a pre-manufactured bend at the flat spring to facilitate installation of the brace onto the user's foot.

17. The hallux valgus brace of claim 16 wherein:
the insert (112) is made of spring steel and provided with a pre-manufactured bend, the degree of the angle of which is about 100° (one-hundred degrees) instead of a right angle; and
in the flexed configuration, the pry arm and lever arm are flexed to close the angle to about 90°, whereby the spring-steel insert (112) is flexed by just about 10° and which is sufficient to generate a sufficient restoring moment (R) on the big toe.

18. The hallux valgus brace of claim 1 wherein:
in the flexed configuration, the pry arm extends from the respective junction therefor with flat spring to a lower edge;
said pry arm further comprising an index-toe angle stop (126) extending laterally outward from said lower edge and configured for assisting prevention of the tip of the index toe from submarining under the pry arm and tip of the big toe.

19. A hallux valgus brace to be worn on a user's foot inside a shoe having a toe cap; comprising:
- an elongated spring device comprising a composite structure having at least one insert and covering layer covering the insert;
- said elongated spring device further comprising an abbreviated flat spring portion flanked between an elongated lever arm portion and an abbreviated pry arm portion, respectively;
- said pry arm portion being configured to be interposed between a user's big toe and index toe;
- said lever arm portion being configured to be disposed overlying the at least one knuckle of the user's index toe, middle toe and fourth toe, such that said lever arm portion receives downward urging from the toe cap of the shoe;
- said pry arm portion and lever arm portion having at least two relative configurations relative to each other about the flat spring portion, an un-flexed configuration and a flexed configuration;
- said at least one insert having a spring coefficient, and wherein said pry arm portion is cantilevered from the lever arm portion about the flat spring portion such that the insert tends to induce the pry arm portion to return from the flexed configuration for the pry arm and lever arm portions to the un-flexed configuration therefor;
- wherein the un-flexed configuration is characterized by, prior to any flexure of the spring device, the pry arm and lever arm portions defining an angle between each other representing an open extreme;
- wherein the flexed configuration is characterized by, after flexure to close the angle representing the open extreme, an inward restoring force (R) due to the spring coefficient of the insert that is applied by the pry arm portion against the big toe as the shoe's toe cap urges down on the lever arm portion.

20. The hallux valgus brace of claim 19 wherein:
the pry arm portion terminates away from the flat spring portion in a lower edge;
said pry arm portion further comprising an index-toe angle stop (126) extending laterally outward from said lower edge and configured for assisting prevention of the tip of the index toe from submarining under the pry arm portion and tip of the big toe.

* * * * *